(12) United States Patent
Keidar (10) Patent No.: US 11,517,366 B2
(45) Date of Patent: Dec. 6, 2022

(54) ADAPTIVE AND SELF-ADAPTIVE PLASMA CANCER THERAPEUTIC PLATFORM

(71) Applicant: The George Washington University, Washington, DC (US)

(72) Inventor: Michael Keidar, Baltimore, MD (US)

(73) Assignee: The George Washington University, Washington, DC (US)

( * ) Notice: Subject to any disclaimer, the term of this patent is extended or adjusted under 35 U.S.C. 154(b) by 398 days.

(21) Appl. No.: 16/492,888

(22) PCT Filed: Mar. 13, 2018

(86) PCT No.: PCT/US2018/022240
§ 371 (c)(1),
(2) Date: Sep. 10, 2019

(87) PCT Pub. No.: WO2018/170000
PCT Pub. Date: Sep. 20, 2018

(65) Prior Publication Data
US 2020/0069355 A1    Mar. 5, 2020

Related U.S. Application Data

(60) Provisional application No. 62/470,676, filed on Mar. 13, 2017.

(51) Int. Cl.
*A61B 18/04* (2006.01)
*A61N 2/00* (2006.01)
(Continued)

(52) U.S. Cl.
CPC ............ *A61B 18/042* (2013.01); *A61N 2/002* (2013.01); *H05H 1/40* (2013.01);
(Continued)

(58) Field of Classification Search
CPC ........ A61B 18/042; A61B 2018/00446; A61B 2018/00583; A61B 2018/00642;
(Continued)

(56) References Cited

U.S. PATENT DOCUMENTS 9,521,736 B2 * 12/2016 Jacofsky .................. A61N 1/44
2010/0145253 A1 * 6/2010 Gutsol ................. H05H 1/2406
606/49

(Continued)

FOREIGN PATENT DOCUMENTS

WO    WO 2017/004080 A1    1/2017

OTHER PUBLICATIONS

Wu et al. (1996). Mechanism of Hydrogen Peroxide and Hydroxyl Free Radical-Induced Intracellular Acidification in Cultured Rat Cardiac Myoblasts. Circulation Research, 78(4), 564-572 https://doi.org/10.1161/01.RES.78.4.564. (Year: 1996).*

(Continued)

*Primary Examiner* — Daniel W Fowler
*Assistant Examiner* — Lindsay Regan Lancaster
(74) *Attorney, Agent, or Firm* — Nixon Peabody LLP (57) ABSTRACT

A method and system of adaptive cold atmospheric based treatment for diseased tissues, such as an area with cancerous cells, is disclosed. A plasma device generates a cold atmospheric plasma jet directed at the area having cancerous cells. A sensor is operable to sense the viability of the cancerous cells in the area. A controller is coupled to the plasma device and sensor. The controller is operative to control an initial plasma jet generated by the plasma device. The controller receives a sensor signal from the sensor to determine cell viability of the selected cells from the initial plasma jet. The controller adjusts the plasma jet based on the viability of the cancerous cells.

22 Claims, 8 Drawing Sheets

(51) Int. Cl.
  *H05H 1/40* (2006.01)
  *A61B 18/00* (2006.01)
  *B82Y 5/00* (2011.01)
  *B82Y 25/00* (2011.01)

(52) U.S. Cl.
  CPC ........... *A61B 2018/00446* (2013.01); *A61B 2018/00583* (2013.01); *A61B 2018/00642* (2013.01); *A61B 2018/00839* (2013.01); *A61B 2018/00863* (2013.01); *B82Y 5/00* (2013.01); *B82Y 25/00* (2013.01)

(58) Field of Classification Search
  CPC ........... A61B 2018/00839; A61B 2018/00863; A61N 2/002; A61N 2/00; H05H 1/40; B82Y 5/00; B82Y 25/00
  See application file for complete search history.

(56) References Cited

U.S. PATENT DOCUMENTS

| | | | | |
|---|---|---|---|---|
| 2011/0279944 | A1* | 11/2011 | Seeney | A61N 2/12 361/147 |
| 2013/0137944 | A1* | 5/2013 | Jeong | A61B 5/0068 600/431 |
| 2013/0199540 | A1* | 8/2013 | Buske | A61B 18/042 128/845 |
| 2013/0345620 | A1 | 12/2013 | Zemel | |
| 2016/0001052 | A1 | 1/2016 | Zucker | |
| 2016/0138006 | A1 | 5/2016 | Canady | |
| 2017/0354453 | A1* | 12/2017 | Krasik | A61B 18/042 |

OTHER PUBLICATIONS

Phaniendra, A., Jestadi, D. B., & Periyasamy, L. (2015). Free radicals: properties, sources, targets, and their implication in various diseases. Indian journal of clinical biochemistry : IJCB, 30(1), 11-26. https://doi.org/10.1007/s12291-014-0446-0 (Year: 2015).*
Yang, M. and Brackenbury, W.J., "Membrane potential and cancer progression," Frontiers in physiology, v.1, 185 (2013).
Chen, Z. et al., "In Vitro Demonstration of Cancer Inhibiting Properties from Stratified Self-Organized Micro-Discharge Plasma-Liquid Interface," arXiv:1701.01655, Soft Matter, in review.
Cheng, X. et al., "The Effect of Tuning Cold Plasma Composition on Glioblastoma Cell Viability," PLoS One, 9(5), e98652, May 30, 2014.
Cheng, X. et al., "Synergistic Effect of Gold Nanoparticles and Cold plasma on Glioblastoma Cancer Therapy", J. Phys. D: Applied Physics, 47 (2014).
Yan, D. et al., "Toward understanding the selectivanti-cancer capacity of cold atmospheric plasma—a model based on aquaporins," Biointephases, 10, 040801 (2015).
Keidar, M., "Therapeutic Approaches Based on Plasmas and Nanoparticles," Journal of Nanomedicine Research, Invited Editorial, 3(2): 00052 (2016).
International Search Report in International Patent Application No. PCT/US2018/022240, dated Jun. 20, 2018 (2 pages).

* cited by examiner

FIG. 9

ADAPTIVE AND SELF-ADAPTIVE PLASMA CANCER THERAPEUTIC PLATFORM

PRIORITY CLAIM

The present application claims priority to PCT Application No. PCT/US2018/022240 filed on Mar. 13, 2018, which claims priority to U.S. Provisional Ser. No. 62/470,676, filed Mar. 13, 2017. The entireties of these applications are hereby incorporated by reference.

STATEMENT OF GOVERNMENT SUPPORT

The subject matter of this application was made with support from the United States government under a contract awarded by the National Science Foundation, Grant Number 1465061. The United States government has certain rights in the invention.

TECHNICAL FIELD

The present invention relates generally to cold atmospheric plasma-based treatment systems, and more particularly, to using an adaptive cold atmospheric plasma system for treatments.

BACKGROUND

Cancer is a well-known health issue. There is a large amount of research geared toward effective treatment of cancer. One area of the research has been directed toward methods of eradicating cancerous cells. Plasma is an ionized gas that is typically formed in high-temperature laboratory conditions. Recent progress in atmospheric plasmas has led to cold atmospheric plasma (CAP) devices with an ion temperature close to room temperature. The unique chemical and physical properties of cold atmospheric plasma have enabled its recent utilization in various biomedical applications including cancer therapy. Under certain conditions, plasmas are known to be able to self-organize. Thus, improvements in plasma application in cancer therapy based on this unique plasma attribute are desirable.

Nature consists of various types of patterns and coherent structures, which prevail at different scales from microscopic organisms and colonies, snowflakes, crystals, to galactic. To explain various phenomena associated with pattern formation W. Ross Ashby proposed the so-called "principle of self-organization." It was suggested that a dynamic system, independently of its type or composition, always tends to evolve toward a state of equilibrium, or an attractor. Such tendency leads to reducing the uncertainty about the system's state, and therefore to reduction of the system's statistical entropy. Self-organization is complex and fascinating phenomena commonly observed in both natural and technological settings, within diverse varieties of physics, chemistry, and biology.

Self-organization in plasmas interacting with surfaces is of interest not only from a fundamental point of view, as intrinsic and fascinating characteristics of nature, but also from a practical standpoint in current and emerging technological applications. One of such examples is plasma medicine, a new, largely unexplored multi-disciplinary scientific field that involves physics, chemistry, engineering, and biology. It focuses on the interaction of cold atmospheric plasma (CAP) with soft matter (liquids, cells, tissue etc.). CAP provides a unique, rich environment of reactive oxygen species (ROS), reactive nitrogen species (RNS), charged particles, photons, and electric fields. Assembling these species in various combinations provides an unprecedented possibility to activate specific signaling pathways in cells. Recently many groups around the world reported that CAP can selectively eradicate cancer cells in vitro, while preserving normal cells; and it also significantly reduces tumor size in vivo. CAP selectivity is one of the most intriguing aspects of interaction with cancer and normal cells.

However, the most interesting and important aspects of plasma, i.e., its ability to self-organize has never been explored in biomedical engineering applications. The formation of self-organized patterns in plasmas as a result of instability and bifurcation could lead to formation of coherent structures. These coherent structures tend to modulate plasma chemistry and composition, including reactive species, the electric field, and charged particles. It has been suggested that adaptive plasma techniques may be based on the ability to change plasma composition and key plasma parameters (such as density and temperature) on demand, dependent on specific application and needs.

There is therefore a need for a cold atmospheric plasma system that may be used for cancer therapy for different types of cancer cells. There is a further need for a cold adaptive plasma system using feedback to adjust parameters for the application of the plasma. There is also a need for a cancer treatment system that applies cold adaptive plasma either in vivo or in vitro to a tissue area.

SUMMARY

One disclosed example is a system for treatment of an area having cells. The system includes a plasma device to generate a cold atmospheric plasma jet directed at the area having cells. A sensor operable to sense the viability of selected cells in the area is provided. A controller is coupled to the plasma device and the sensor. The controller is operative to control an initial plasma jet generated by the plasma device. The controller receives a sensor signal from the sensor to determine cell viability of the selected cells from the initial plasma jet. The controller adjusts the plasma jet based on the viability of the selected cells.

Another disclosed example is a method of treating an area having cells. A gas is ionized to create an initial cold atmospheric plasma jet. The initial plasma jet is directed toward the area. The cell viability of selected cells in the area is determined based on sensing the area. The plasma jet is adjusted based on the determined cell viability of the selected cells.

Another disclosed example is a system for treatment of an area having cancerous cells. The system includes a plasma device to generate a cold atmospheric plasma jet directed at the area having cancerous cells. A marker material is provided in the area. The marker material produces a luminescence level relative to the viability of the cancerous cells. The system includes a luminescence sensor and a controller coupled to the plasma device and luminescence sensor. The controller is operative to control an initial plasma jet generated by the plasma device. The controller measures the luminescence of the markers in the area to determine cell viability from the initial plasma jet. The controller adjusts the plasma jet based on the determined cell viability.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims.

DETAILED DESCRIPTION

The present inventions can be embodied in many different forms. Representative embodiments are shown in the drawings, and will herein be described in detail. The present disclosure is an example or illustration of the principles of the present disclosure, and is not intended to limit the broad aspects of the disclosure to the embodiments illustrated. To that extent, elements and limitations that are disclosed, for example, in the Abstract, Summary, and Detailed Description sections, but not explicitly set forth in the claims, should not be incorporated into the claims, singly or collectively, by implication, inference, or otherwise. For purposes of the present detailed description, unless specifically disclaimed, the singular includes the plural and vice versa; and the word "including" means "including without limitation." Moreover, words of approximation, such as "about," "almost," "substantially," "approximately," and the like, can be used herein to mean "at," "near," or "nearly at," or "within 3-5% of," or "within acceptable manufacturing tolerances," or any logical combination thereof, for example.

In reference to the below examples, an adaptive system is a system that is able to change its function in response to its environment. Aquaporin is a membrane protein that promotes the transfer of water and other large molecules.

Plasma is an ionized gas that contains charged particles (ions and electrons). Plasma discharge is the transmission of electricity through ionized gas. A sheath is a layer adjacent to the plasma boundary that is the result of charged particle separation.

Self-organization in plasmas can be described as a process of spontaneous transition from a homogeneous stable state to a regular pattern in a spatially extended system or a transition between different patterns. Different types of self-organization phenomena have been reported in a wide range of plasma discharges, such as dielectric barrier discharge, high-frequency discharge, gas flow stabilized discharges, resistively stabilized discharges, and discharges with liquid electrode. In many situations pattern formation is the result of a nonlinear interaction of the plasma with the electrode surfaces. It has also been shown that a 3D collective motion of plasma filaments can be observed. When liquid (water) acts as a cathode, the 3D configuration of the discharge luminance self-modulates from an axial symmetrical horn to a rectangular horn accompanied by a symmetrical degree of freedom. The non-linear evolution of argon discharge above a water electrode has also been investigated. The charged particle bombardment process is probably responsible for the differing behaviors of the microdischarges when the water acts as cathode or anode. A self-rotating, low-current atmospheric discharge between a metallic cathode and a water anode gives rise to a ring-like anode spot. Inter-electrode spacing, electrolyte composition/concentration, current, and the diameter of the metal cathode affect the discharge self-organization patterns. In AC-driven discharges between a metal disc and a water electrode, distinctive patterns depend on the polarity of the electrodes. In general, contact of plasma with surfaces including liquids and biological objects leads to the formation of a transition layer or sheath. Sheath formation might be considered one of the best-known self-organization phenomena. Overall, the plasma-surface interface is structured into several sub-regions characterized by different space charges and electric fields, such as the sheath. Thus, self-organization in plasmas may form coherent structures that modulate plasma chemistry and composition, including reactive species, the electric field, and charged particles. Such modulation of plasma composition could be utilized in an adaptive plasma device that may more effectively offer treatment for cancerous cells.

Figure 1A:
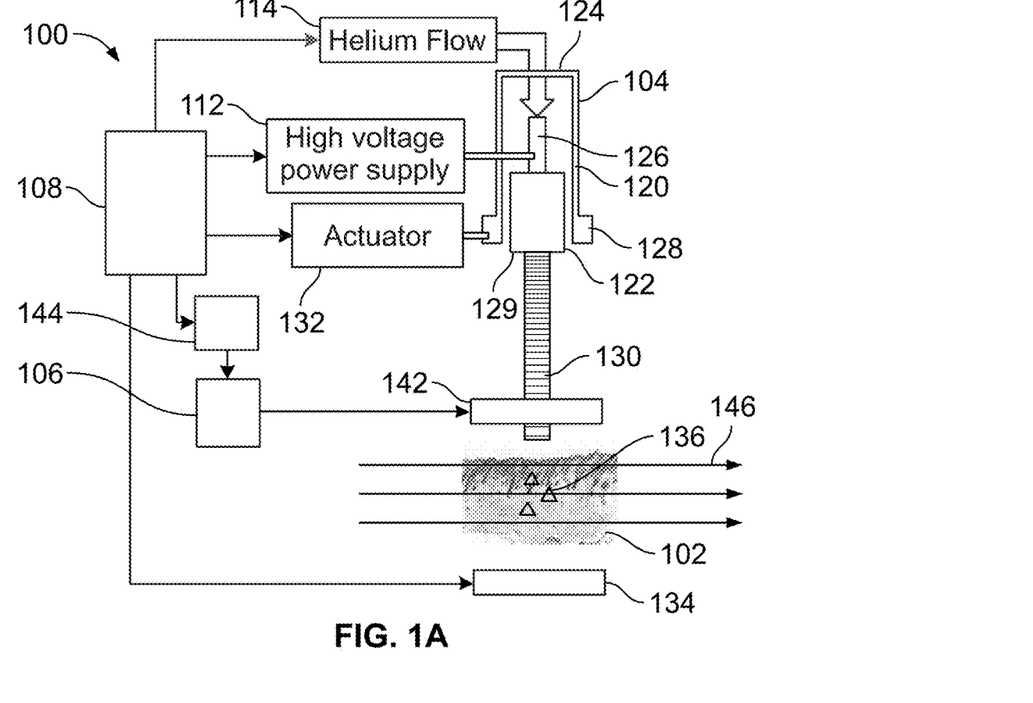
FIG. 1A is a block diagram of an adaptive in vivo system for treatment of an area with cancer cells with a plasma jet and a magnetic field.

FIG. 1A is a block diagram of an in vivo cancer treatment system 100 that subjects an area of cancerous cells on a patient 102 to a cold atmospheric plasma jet and a magnetic field. The system 100 includes a cold atmospheric plasma emitter device 104 and a magnetic field generator 106. A controller 108 allows a user to control the cold atmospheric plasma to selectively treat cancer cells. As will be explained, the controller 108 is operative to allow adaptive application of the cold atmospheric plasma jet from the emitter device 104 based on real time feedback from the area of cancerous cells. Thus, the controller 108 allows adaptive control of the plasma jet to increase eradication of cancerous cells while decreasing damage to normal cells.

The cold plasma emitter device 104 includes a power supply 112, a gas source 114, and a delivery mechanism 120. In this example, the delivery mechanism 120 is an elongated syringe having a main body 121. The main body 121 may be made of glass or a rigid plastic, but also can be made of a flexible material. A proximal end of the body 121 is sealed with a sealing plug 124 and an opposite distal end has a discharge area 122. The distal discharge end 122 of the syringe body 121 has a narrowed neck and a distal opening or nozzle 129. A central electrode 126 is located at the center of the body 121 at the interior of the body 121 at the central longitudinal axis of the syringe 120. The central electrode 126 enters the syringe 120 at the sealed proximal end of the body 121 and extends the length of the body 121 to approximately the discharge end 122. The sealing plug 124 (which may be rubber) is located over the open end of the syringe 120 to prevent the gas from escaping from the inside of the syringe 120. The electrode 126 is entirely surrounded by insulation except at its distal end, which is exposed and in contact with gas and plasma. The insulation allows the power to be focused at the exposed distal end of the electrode 126 to lead to the discharge at the end. The central electrode 126 and surrounding insulation, has a proximal end that extends to the outside of the syringe 120 through an opening in the plug 124. The plug opening forms a friction fit with the insulation, so that gas does not escape from the syringe 120. The central electrode 126 is positioned inside the body 121 of the syringe 120, except for the portion of the proximal end of the electrode 126 that extends into and through the plug 124.

In this manner, the plug opening holds the electrode 126 and insulation in position within the syringe 120, with the distal end of the electrode 126 facing the distal nozzle 129 of the syringe body 121. In addition, an annular outer ring electrode 128 is located about a portion of the narrow neck at the outside of the syringe 120. The electrodes 126 and 128 are high voltage electrodes. The central electrode 126 may be, for instance, a wire, and the insulation can be a ceramic insulation. The high voltage power supply 112 is electrically connected to the electrodes 126 and 128 and provides a high voltage supply to the electrodes 126 and 128 through cables. The controller 108 is coupled to the high voltage power supply 112 and regulates the discharge voltage and frequency that is applied to the central electrode 126 and the ring electrode 128 and therefore controls the intensity of a plasma jet 130 emitted by the nozzle 129. Alternatively, the controller 108 may regulate the discharge current to regulate the plasma jet via the power supply 112.

The gas source 114 is in gas communication with the delivery device 120 through a supply tube. The supply tube is connected to a port located on the plug 124 of the syringe 120. The supply tube 118 may also be connected to the syringe 120 through an adapter. The gas source 114 can be pressurized, so that gas travels through the supply tube 118 into the inside space of the syringe body 121. A separate gas controller (not shown) may be provided to control the flow rate of the gas in the supply tube 118, or the gas controller may be integrated with the controller 108. The gas then continues through the syringe 120 and exits the syringe 120 through the neck and nozzle 129 at the discharge end 122 as the jet or stream flow 130. The gas source 114 may include multiple gas sources for mixtures of different gases such as helium, argon, and nitrogen. The controller 108 or separate gas controller can also control gas composition in the example of multiple gas sources as well as the flow rate of the gasses in the composition.

As the gas enters the discharge area 122 and the neck of the syringe 120, the electrodes 126 and 128 excite the gas, thereby ionizing the gas to form a cold plasma jet. In this example, the gas is helium, though other gases such as nitrogen may be used. Thus, as the gas is discharged out of the distal nozzle 129 of the syringe 120, it is a cold plasma jet. The cold plasma jet or stream flow 130 diffuses over time. In accordance with this example, the plasma is provided at a flow rate of 17 liters per minute, with the voltage supply being 5 kV and at 30 kHz. At that configuration, the plasma will have a high ionization as it exits the syringe 120.

Accordingly, the syringe 120 is preferably placed at a predetermined distance from the target cells of the patient 102 being treated.

The syringe 120 allows the plasma to be targeted at desired cancer cells in the skin to selectively eradicate the cancerous cells and reduce tumor size. The syringe 120 may be utilized, for instance, to treat any cancer type that is close to the skin and can be applied without surgery, such as for breast, colon, lung, bladder, or oral cancers. With surgery, the system 100 may be applied to any tumor. In this example, the flow rate may be 10-17 liters/min., with a voltage of 2-5 kV and a frequency of 10-50 KHz. Of course, other flow rates, voltages, currents, and frequencies may be used. For example, in the case of localized treatment, a flow rate of 0.1 liters/min. may be used. The nozzle 129 may be between 3-5 mm diameter and the distance between the central electrode 126 and the ring electrode 128 may be 5-10 mm. At the predetermined distance, the plasma will have diffused to a desirable level. However, the intensity of the plasma will continue to decrease as the target area is moved further from the syringe 120, and the plasma will be essentially entirely dissipated at a distance of 5 cm from the syringe 120 in this example. The plasma is well collimated the entire length up to about 5 cm from the syringe 120. The plasma jet stream is discontinuous and represents a series of propagating plasma bundles. In this example, a mechanical actuator 132 may be deployed to move the location of the syringe 120 and thereby change the predetermined distance between the syringe 120 and the target area. The mechanical actuator 132 is controlled by the controller 108.

The controller 108 is also coupled to a sensor to sense the area to determine the viability of the cancerous cells. The controller 108 determines the viability from the sensor data as feedback from the plasma jet and adjusts the plasma jet accordingly in response to the feedback. In this example, the sensor to sense cancer cell viability is a luminescence sensor 134. The luminescence sensor 134 provides luminescence data from the area of cancerous cells based on an injected marker material 136 and thus provides real time feedback as to the effect of the plasma jet 130 on the cancerous cells as will be explained below in reference to FIG. 6. As will be explained below, the controller 108 may be used to control distance, power supply, and gas flow to adapt the plasma jet 130 to maximize the treatment of the patient 102.

The magnetic field generator 106 includes an electromagnet 142 that is coupled to a power regulator 144 to generate a magnetic field 146 around the area of the patient 110. The electromagnet 142 may be moved to focus the magnetic field in the area where the plasma jet stream 130 from the syringe 120 is focused. The strength of the magnetic field 146 may be controlled by the controller 108. The magnetic field is an optional feature that serves to assist in the eradication of cancer cells by the plasma jet.

Figure 1B:
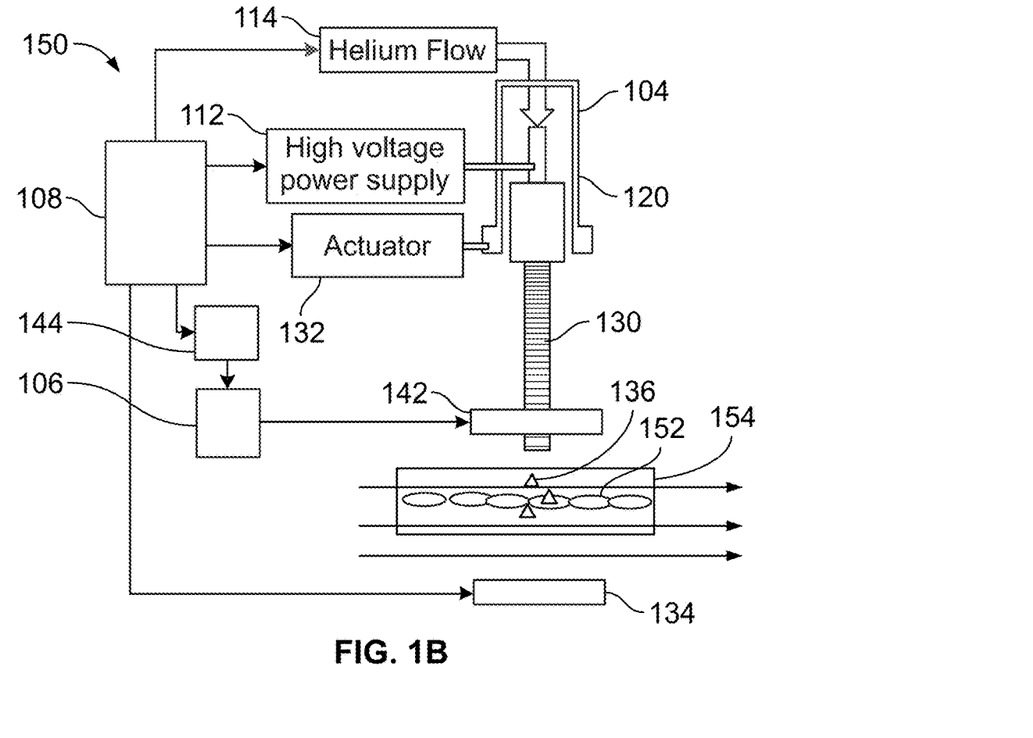
FIG. 1B is a block diagram of an adaptive in vitro system for eradication of cancer cells with a plasma jet and a magnetic field.

FIG. 1B shows an in vitro system 150 that may be used in conjunction with cells 152 that are contained in a tray 154. The in vitro system 150 may be used for testing treatment parameters or study of cell explant from patient. In this case cells will be treated in order to determine a personalized approach for specific patient. The cell explant may be obtained via a biopsy. Various components in the in vitro system 150 are identical to those of the in vivo system 100 in FIG. 1A and like elements are labeled with identical element numbers. A controller 108 allows control of the plasma device 104 to deliver the plasma jet 130 to the cells 152 in the tray 154. The controller 108 also controls the magnetic field generator 106 to generate the magnetic field 146 through the electro-magnet 142. In this manner, the cells 152 are subjected to exposure to the plasma jet 130 and the magnetic field 146.

Figure 1C:
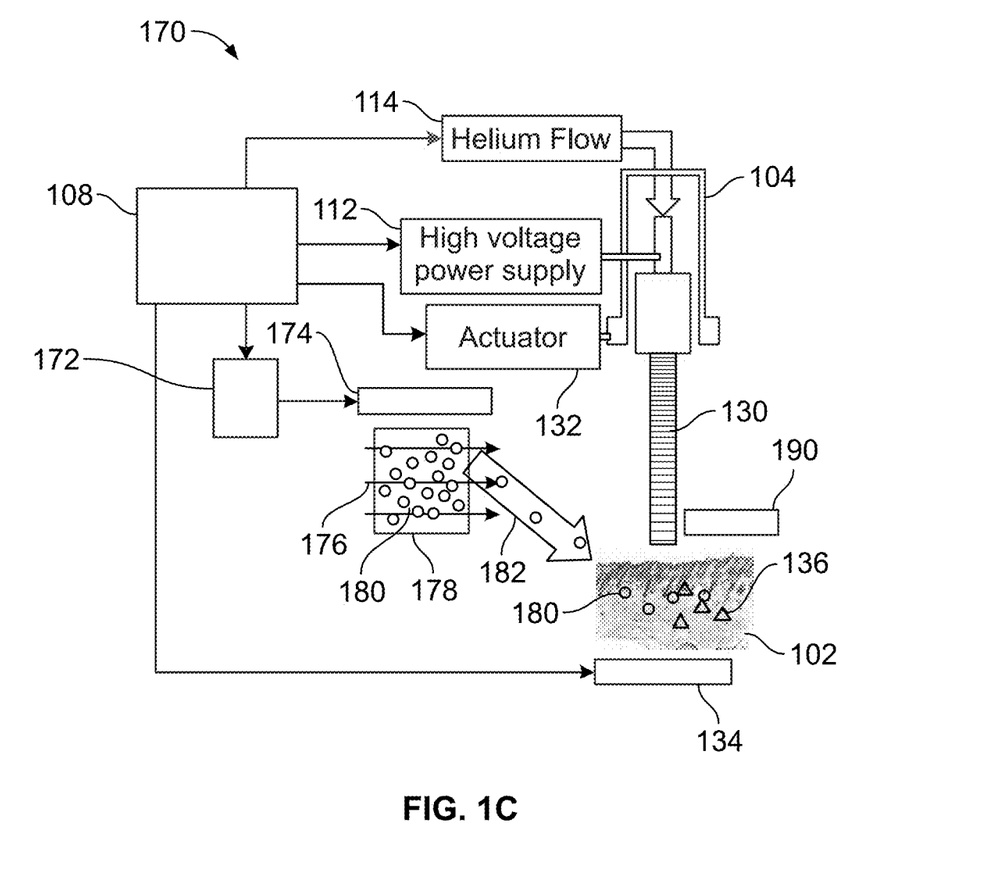
FIG. 1C is a block diagram of another adaptive in vivo system for treatment of an area having cancer cells with a plasma jet and magnetic nanoparticles.

FIG. 1C shows a treatment system 170 using magnetic nanoparticles to deliver a magnetic field to the patient 102 in conjunction with a cold atmospheric plasma jet. The cold plasma emitter device 104 is identical to that in FIG. 1A and thus like elements are labeled with like element numbers. As explained above, the plasma emitter device 104 emits a plasma jet 130 directed toward the area of the patient 102 that has a concentration of cancerous cells.

The controller 108 is coupled to a magnetic field generator 172 that controls an electromagnet 174. The electromagnet 174 generates a magnetic field 176 in a particle chamber 178. The particle chamber 178 holds nanoparticles 180 that are magnetized by the magnetic field 174. The magnetized magnetic nanoparticles 180 are delivered to the area of the patient 102 via an injector 182. The magnetic nanoparticles 180 are thus delivered to emit a magnetic field on cancerous cells in conjunction with the plasma jet 130.

The treatment system 170 allows generating the magnetic field in areas with high concentrations of cancerous cells. Thus, the effect of the magnetic field on surrounding areas with normal cells is bypassed. The magnetic nanoparticles 180 target only the cancer cells in the injection region. The magnetic nanoparticles 180 may be further guided by a magnet 190 to a specific location for a more focused treatment. Alternatively, the magnetic nanoparticles 180 may be conjugated with a targeting antibody that may be injected in the area of cancerous cells. Such an arrangement may allow a synergetic effect of plasma, magnetic field, and a drug carried by the magnetic nanoparticles.

The systems shown in FIG. 1A-1C are each an adaptive plasma therapeutic system. Thus, each system includes a plasma device such as the plasma emitter 104 that is capable of adjusting the composition of the cold atmospheric plasma to obtain optimal outcomes through its interaction with soft matter. The adjustment may be performed by the controller 108 by adjusting the distance of the plasma source by the actuator 132, the gas flow, and gas composition via the gas source 114, or the power of the plasma source by the voltage power supply 112 for example. Biological response of living tissue may be recorded using a variety of imaging tools, as well as chemical and biological reporters such as the markers that produce levels of luminescence detected by the luminescence sensor 134. Such feedback mechanisms enable adaptive features of a plasma-based therapeutic system via the controller 108. Self-organization in plasmas produced by the adaptive systems may lead to the formation of coherent structures. These coherent structures tend to modulate plasma chemistry and composition, including reactive species, the electric field, and charged particles. Such modulation of plasma composition could be utilized by the adaptive plasma devices described in FIGS. 1A-1C.

Emerging evidence of the adaptive cold atmospheric plasma (CAP) jet effectiveness in the selective killing of cancer cells and decreasing tumor size provides a solid basis for its use in cancer treatment. Experiments to date demonstrate a potent effect of CAP treatment on GBM cancer cells in vitro, while minimal effect was seen on normal human astrocytes. Most importantly, these findings are translated into an in vivo animal model with mouse xenografts, with CAP treatment eliciting a marked reduction in tumor volumes using an intracranial glioblastoma (GBM) model. An example process of operating an adaptive cold atmospheric plasma system is shown schematically in FIG. 2A. The process illustrated in FIG. 2A could use any adaptive cold plasma system such as those shown in FIGS. 1A-1C above.

Figure 2A:
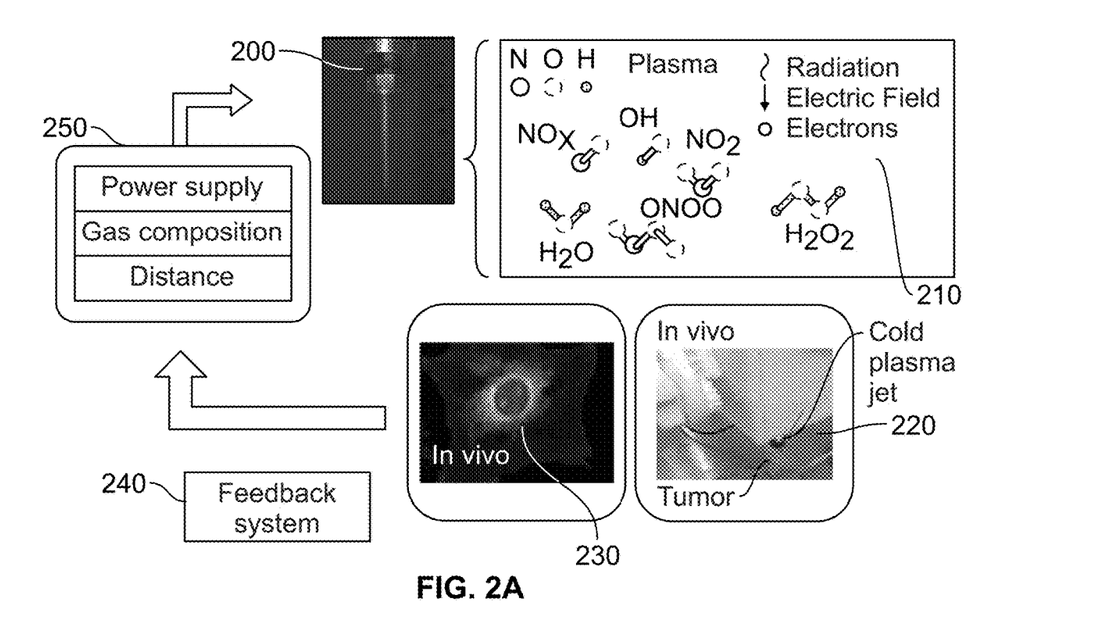
FIG. 2A is a flow diagram of the operational process of using an adaptive cold plasma system such as those systems shown in FIGS. 1A-1C.

The procedure shown in FIG. 2A allows cold plasma composition and power to be adapted based on cellular and tissue responses. FIG. 2A shows a cold plasma beam apparatus 200. The apparatus 200 produces a plasma jet 210 composed of hydrogen injected into atmospheric gases of nitrogen and oxygen. As explained above, the apparatus 200 may be applied for an in vivo application (220) or an in vitro application (230) to an area with cancer cells. A feedback system 240 may determine the effectiveness in eradication of the cancer cells in the area of interest. To this end, various markers can be used such as RealTime-Glo™ MT by Promega Corporation in the area of interest to demonstrate the effect of the beam on the cancer cells. As explained above, the luminescence of the markers may be detected by the luminescence sensor 134 and input to the controller 108 in FIGS. 1A-1C. Adjustments may be made to inputs including the power supply, gas composition, or distance of the jet to the area of interest based on the feedback from the markers in the cells (250). Such adjustments may include changing the power supply via a voltage supply such as the voltage supply 112, the gas composition and gas flow via the gas source 114, and the distance between the jet and the area of interest via the mechanical actuator 132 in FIGS. 1A-1C.

Thus, the process in FIG. 2A shows reading the cellular response to cold adaptive plasma in real time via sensor data from the cellular response and modifying the plasma composition and power via a feedback mechanism such as those shown in FIGS. 1A-1C operated by the controller 108. This process allows for modification of the plasma conditions in real time to optimize the cold plasma effect on cancer cells in the area of interest. In addition, due to a distinct effect of cold plasma on normal cells and cancer cells, such a system can lead to enhanced selectivity of the plasma by controlling the generation of reactive species or the potential interaction between the cold atmospheric plasma and cells.

Figure 2B:
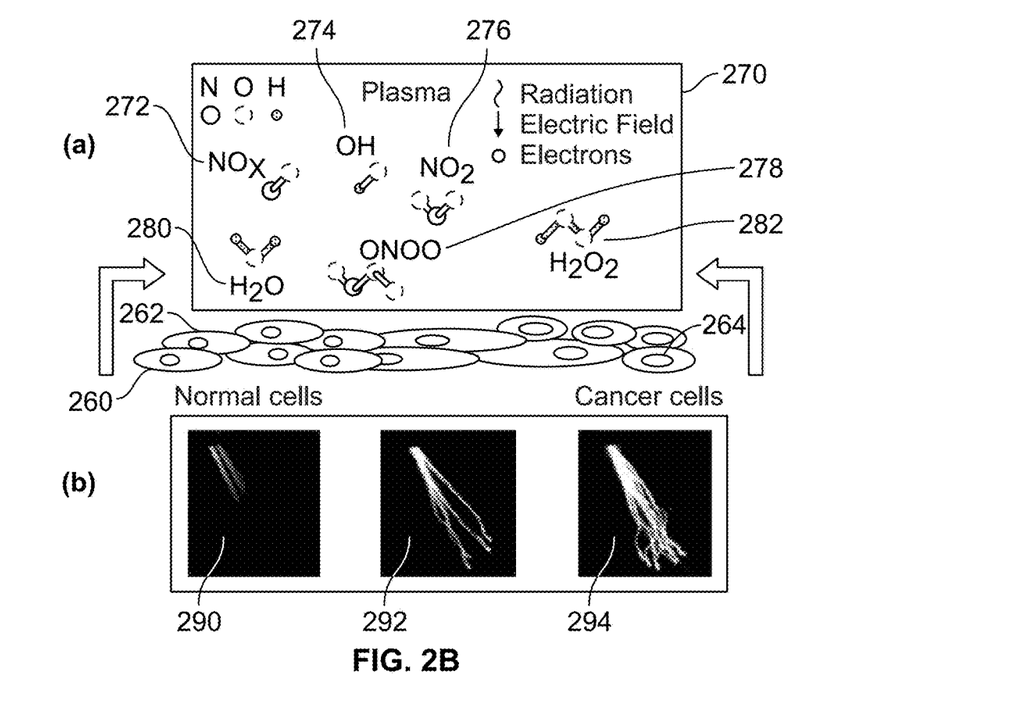
FIG. 2B is a diagram showing how plasma interaction with cells leads to plasma transition between different plasma discharge modes.

FIG. 2B shows an area of interest 260 that includes normal cells 262 and cancer cells 264. As shown in FIG. 2B, a plasma stream 270 includes NOx molecules 272, OH molecules 274, $NO_2^-$ molecules 276, $ONOO^-$ molecules 278, $H_2O$ molecules 280, and $H_2O_2$ molecules 282 that are produced by the plasma reaction with atmospheric gas. In this example, the molecules 272, 274, 276, 278, 280, and 282 are formed by the plasma discharge. Certain molecules such as the $ONOO^-$ molecules 278 and $H_2O_2$ molecules 282 are nitrogen and oxygen reactive species that react with the cells 262 and 264. In this example, the $H_2O_2$ molecules 282 are the most reactive species. FIG. 2B shows schematically how the plasma interaction with cells can lead to plasma transition between different plasma discharge modes thus providing the possibility for plasma self-adaptation. Thus, the uniqueness of plasma is its ability to change its composition and key parameters on demand, dependent on specific requirements. Using nanoparticles in a system such as that shown in FIG. 1C can accurately localize the plasma treatment effect. Gold nanoparticles in particular can enhance the plasma-mediated effect, while at the same time plasma can enhance nanoparticle-based drug delivery. The plasma composition can be affected by discharge conditions such as gas flow rate and power.

Specifically, FIG. 2B shows the cold plasma discharge is affected by normal cells 262 and cancer cells 264. Cancer and normal cells have significant differences in membrane potential, which can be used as a signal to trigger plasma self-organization and change the plasma output. This distinct response of plasma to cells and tissue leads to plasma mode transition. The plasma mode transition may be seen in the images 290, 292, and 294. The images 290, 292, and 294 are images of light emissions from plasma organization near the surface of the cells. As shown in the image 294, plasma self-organization triggered from the membrane potential of the cells 264 reacting with the reactive species has changed the plasma organization. An example of the self-adaption effect on cancer cell eradication may be seen in FIG. 7.

Figure 3:
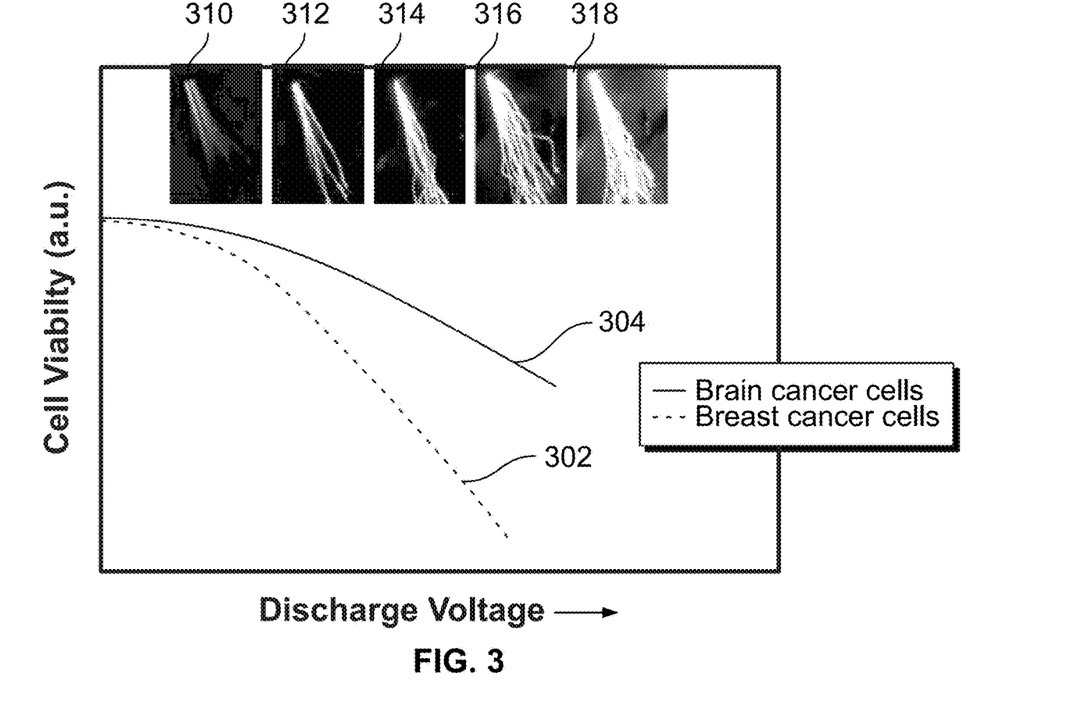
FIG. 3 is a graph of cell viability in relation to different levels of discharge voltage and images of plasma discharge.

As explained above, plasma composition can be affected by discharge conditions such as gas flow rate and power. In general, brain tumor cells are more resistant to plasma treatment than breast cancer cells. The viability of brain tumor cells is affected by plasma treatment to a smaller degree than that of breast cancer cells. Thus, an increase of the discharge voltage or discharge current can lead to stronger effects of cold plasma treatment on more resistant cells such as brain tumor cells. This effect is shown schematically in the graph in FIG. 3 that plots cell viability as a result of plasma treatment in relation to discharge voltage. A first line 302 shows the viability of breast cancer cells at different discharge voltages. A second line 304 shows the viability of brain cancer cells at different discharge voltages. As may be seen in FIG. 3, compared with the gas flow rate, the cold atmospheric plasma (CAP) discharge voltage is the more important factor affecting the death rate of cancer cells and therefore the adaptive therapy system would adjust the discharge voltage for treatment of cancer cells. FIG. 3 also shows a series of images 310, 312, 314, 316, and 318 that show plasma self-organization as discharge voltage increases. As shown by the images 310, 312, 314, 316, and 318, the discharge voltage affects the organization of plasma in a helium discharge above the water.

Consequently, to reach equivalent levels of targeted cell viability, different cancer cell lines each require a unique combination of helium flow rate and discharge power (voltage) for maximum effectiveness of the cold atmospheric plasma treatment. Thus, the outcome of the plasma-cell interaction can be affected by discharge conditions such as gas flow rate and power. For effective plasma cancer treatment, CAP parameters such as gas flow and discharge power are tuned according to the response of tumor cells in situ. The controller 108 in FIGS. 1A-1C adjusts the composition and power of CAP autonomously based on the cellular and tissue response to plasma in real time. This can be achieved by monitoring the spatial distribution and the quantitative degree of cell viability with in situ diagnostics and by determining the optimal composition and power of CAP to minimize the viability of tumor cells with a feedback control algorithm executed by the controller 108. Thus, the treatment of cancerous cells such as brain cancer cells, breast cancer cells, pancreatic cancer cells, skin cancer cells, bladder cancer cells, colon cancer cells, head and neck cancer cells, or lung cancer cells may be enhanced.

One example of in situ cell monitoring is the RealTime-Glo MT Cell Viability Assay offered by Promega Corporation. This assay allows continuous monitoring of cells in culture during a cold atmospheric plasma treatment. This assay involves adding NanoLuc® luciferase and a cell-permeant pro-NanoLuc® substrate to cells in the culture medium. Cells that remain metabolically active reduce the cell-permeant pro-substrate NanoLuc® to generate a substrate for NanoLuc® luciferase, which then diffuses into the culture medium. The pro-substrate is rapidly used by the NanoLuc® enzyme to produce a luminescent signal. The strength of the luminescent signal correlates with the number of cells that remain viable after plasma treatment. Dead cells are unable to reduce the pro-substrate and therefore do not produce a luminescent signal. In this manner the response of the cells to the plasma can be monitored in real time via a luminescence sensor such as the sensor 134 in FIGS. 1A-1C. The cell response differs between cell types based on the duration of CAP treatment and the applied voltage. Cell response (viability) can be monitored and analyzed during or immediately after plasma treatment. If necessary, the plasma composition can be modified (e.g., by adjusting the discharge voltage, distance, gas flow, or gas composition) to achieve a desirable cell viability according to cell type being treated. Moreover, plasma self-organization might be triggered by changes in external parameters (discharge voltage, electrode conductivity, or distance between electrodes, to name but a few).

The images 310, 312, 314, 316, and 318 of plasma shows the discharge voltage can strongly affect plasma self-organization above the liquid electrode. Different discharge patterns shown in the images 310, 312, 314, 316, and 318 result in significant changes in composition and cell viability after plasma treatment. Plasma self-organization is an example of tuning plasma composition and thus the cellular response by external discharge parameters. An alternative way to drive the self-organization process is through the possible feedback effect of cells on plasma near the cell-plasma interface. Among the various effects of cells and tissue on plasma is the electric field at the cell membrane. Different cells of differing membrane surface charge can selectively affect plasma. It is known that rapidly proliferating cancer cells have a depolarized membrane potential. Given that the cell membrane thickness is about 7-9 nm, the electric field is approximately $10^7$ V/m in the case of a normal cell and lower by factor of two to three in the case of cancer cells. Such an electric field might affect both plasma dynamics near the plasma-cell interface and the plasma chemistry. Consequently, the chemical species may be manipulated by applying an electric field on the jet. For example, when the plasma interacts with cells, the amounts of $N_2$, N2+, He, and O can be increased if a low-potential object is placed behind the cell. This is confirmed by cellular tests and an electrical grid simulating the electrical field of different cells.

Figure 4:
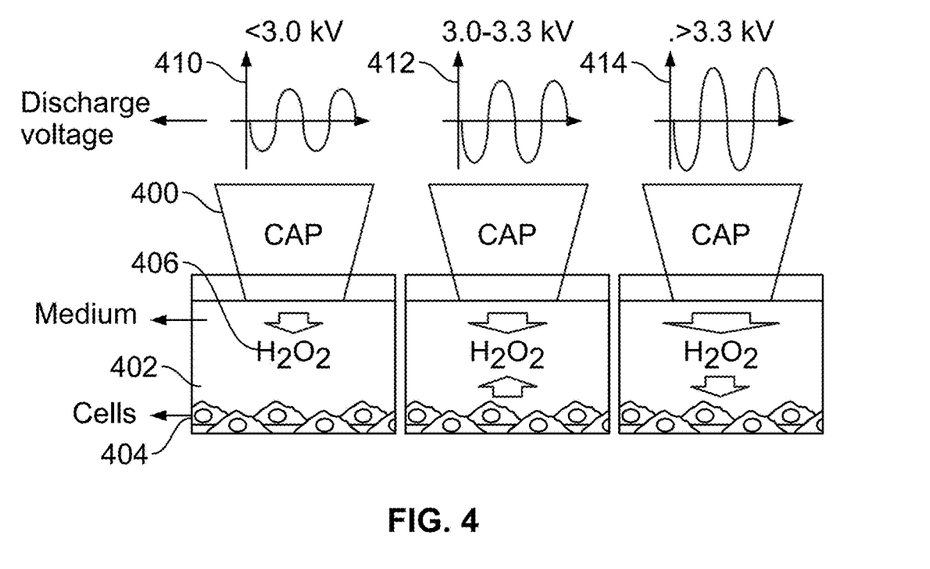
FIG. 4 is a diagram of the effect of different levels of discharge voltage on cells.

Another example may be seen in using an adaptive cold atmospheric plasma system in treatment of breast cancer cells. FIG. 4 shows a CAP jet 400 that is directed toward a medium 402 to cells 404 in an area of interest. In this example, $H_2O_2$ molecules 406 are generated by the plasma reaction.

FIG. 4 shows the application of discharge voltage 410 of less than 3.0 kV, discharge voltage 412 of 3-3.3 kV and discharge voltage 414 of greater than 3.3 kV. As may be seen in FIG. 4, cell-based $H_2O_2$ generation will not occur when the discharge voltage is too low, such as below 3.0 kV. In this case, the $H_2O_2$ in the medium 406 will be provided only by CAP-originated species such as OH. When the discharge voltage continues to increase, cell-based $H_2O_2$ generation will start to be observed. Maximum generation occurs when the discharge voltage is between 3.00 kV and 3.30 kV, such as 3.16 kV. The amount of cell-based $H_2O_2$ generation can be as large as the $H_2O_2$ formed directly from CAP-originated species. As the discharge voltage continues to increase, cells change their role from producers to consumers of $H_2O_2$. The presence of cells 404 in the medium 406 significantly decreases the $H_2O_2$ generated from the CAP jet 400.

Another example feedback mechanism may be associated with the production of $H_2O_2$ by cancer cells during direct CAP treatment, as shown in FIG. 4. The $H_2O_2$ molecules 402 may be formed by some CAP-originated reactive species such as ($OH^-$) in CAP-treated aqueous solutions including a cell culture medium, i.e., $H_2O_2$ molecules is the end product that react with cells. However, at least some cancer cells, such as breast cancer cells (MDA-MB-231) and pancreatic adenocarcinoma cells (PA-TU-8988T), can generate micromolar (μm) levels of $H_2O_2$ during direct CAP treatment of these cells. This unique cellular response to CAP may be due to the superoxide-related dismutation reaction catalyzed by extracellular superoxide dismutase. Superoxide can be provided by the CAP process. $H_2O_2$ cell generation is an immediate response of cells to plasma treatment and as such can be used to assess the effect of plasma on cells in real time. Such μm level cell based $H_2O_2$ generation is a cell type-specific phenomenon. Selective production of hydrogen peroxide by different cells can lead to the adaptation of chemistry at the plasma-cell interface based on the cellular input. Cell-based $H_2O_2$ generation can be easily quantitated by UV-visible spectrometry or using other specific chemical probes for $H_2O_2$ molecules. Online measurement of $H_2O_2$ generation can directly provide information about the cell type. Such information can be a feedback signal to an adaptive CAP device. In particular, the discharge voltage is an important factor that affects the ratio of reactive oxygen species (ROS) to reactive nitrogen species (RNS) and this voltage correlates significantly with the cell-based $H_2O_2$, as shown schematically in FIG. 4 with the different voltage discharge levels 410, 412, and 414. As explained above, cell-based $H_2O_2$ generation will appear only when the input discharge voltage is moderated. A discharge voltage that is either too high or too low can weaken or even completely stop such cell-based $H_2O_2$ generation.

Figure 5:
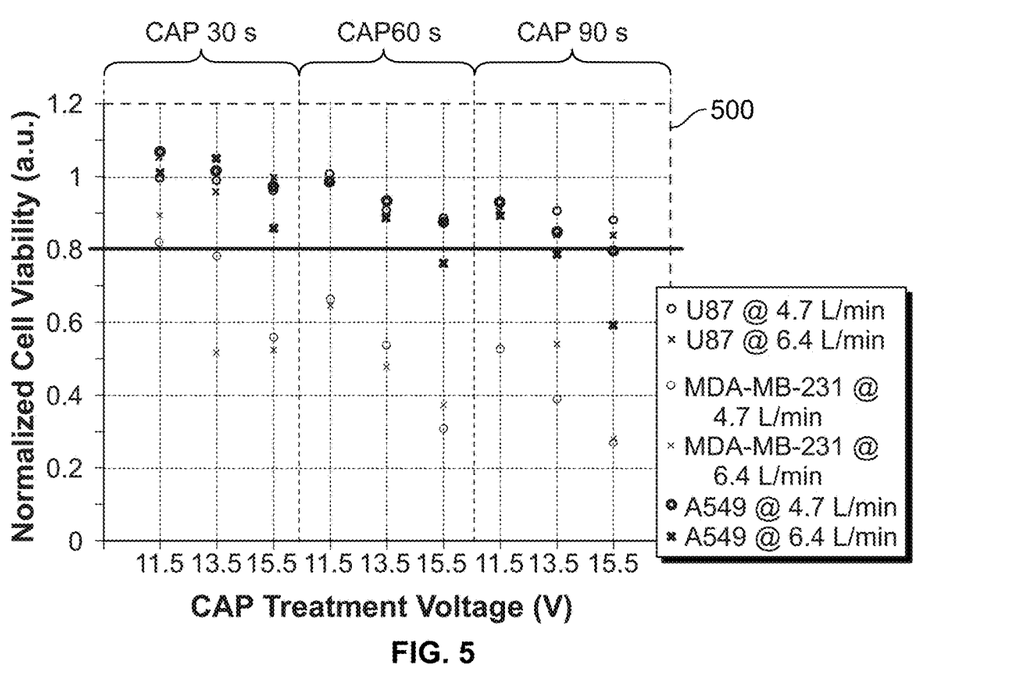
FIG. 5 is a graph that shows cell viability of different cell lines at the different gas flow rates for producing the plasma jet.

FIG. 5 is a graph that shows cell viability of GBM (U87), lung cancer (A549), and breast cancer (MDA-MB-231) cell lines at the same plasma conditions. The graph in FIG. 5 plots normalized cell viability versus the length of cold adaptive plasma treatments. All three types of cell lines were considered at helium flow rates of 4.7 L/min and 6.4 L/min. The U87 and A549 cells are more robust than the MDA-MB-231 cells such that the former requires either an increase in the helium flow rate from 4.7 L/min to 6.4 L/min or a voltage modification to the plasma discharge to reach the same tumor cell kill as seen in the latter. Consequently, there exists a unique combination of helium flow rate and discharge power (voltage) to reach an equivalent targeted cell viability level between the three different cancer cell lines. Thus plasma composition can be affected by discharge conditions such as gas flow rate and power. The adaptive systems described above allow for the adjustment for the optimal gas flow rate and power for the CAP and therefore may provide optimal treatment for particular cells. For example, efficacy of CAP treatment can be adjusted by modifying helium flow rate as well as by adding 50 nm gold nanoparticles such as shown in the system in FIG. 1C.

FIGS. 1A-1C therefore show an adaptive plasma cancer treatment system that adjusts the composition and the power of CAP autonomously, based on the cellular and tissue response to plasma in real time. This is achieved by monitoring the spatial distribution and the quantitative degree of cell viability with in situ diagnostics such as the luminescence sensor 134 and by determining the optimal composition and the power of the CAP to minimize the cell viability of GBM tumors with a feedback control algorithm executed by the controller 108.

Figure 6:
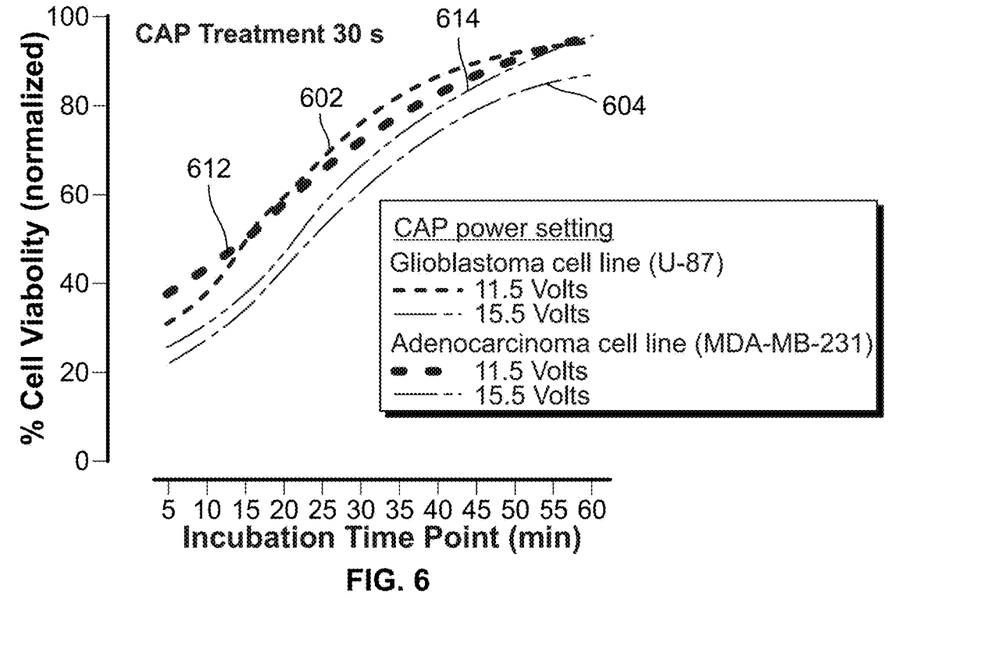
FIG. 6 is a graph that shows an assay demonstrating cell viability based on discharge power.
Figure 7A:
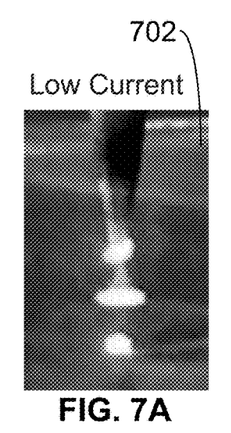
FIG. 7 show graphs of plasma self-organization and time dependencies of concentrations.
Figure 7B:
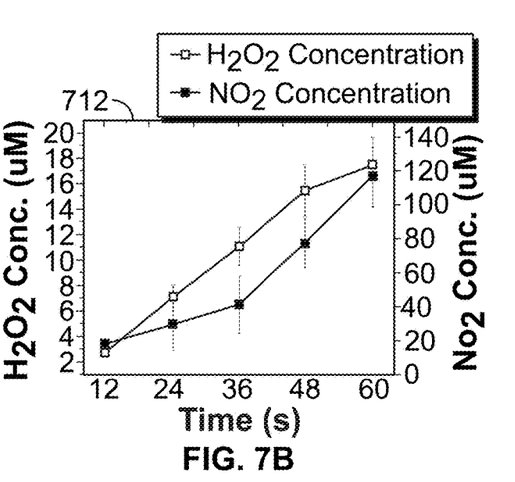
Figure 7C:
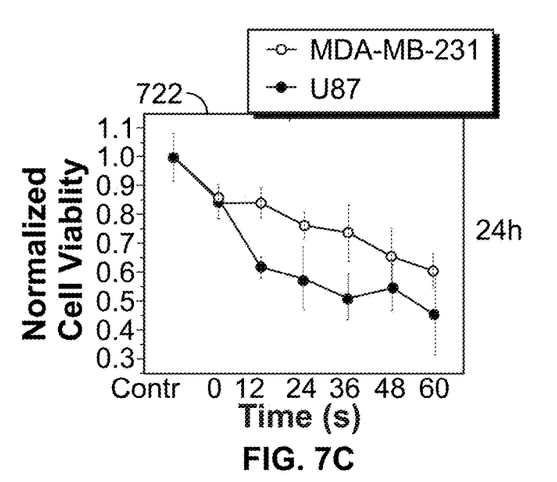
Figure 7D:
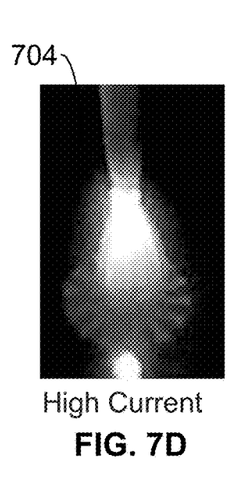
Figure 7E:
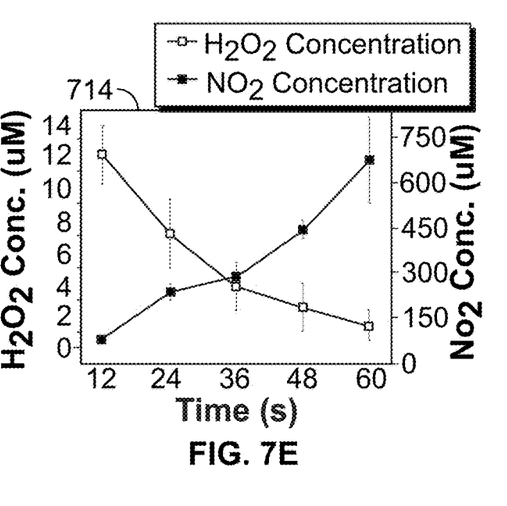
Figure 7F:
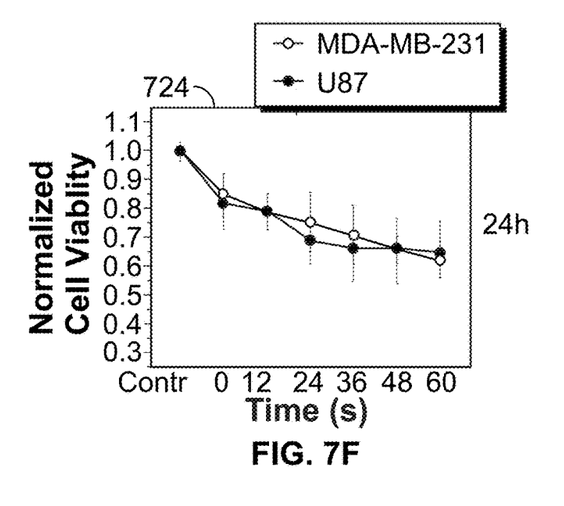

FIG. 6 is a graph of cell viability measured by a real time Glo Luminescence assay that shows dependence on discharge power. A line 602 represents the viability of the Glioblastoma cell line (U-87) at 11.5 volts over incubation time. A second line 604 represents the viability of the Glioblastoma cell line (U-87) at 15.5 volts over incubation time. As shown by FIG. 6, the viability of the Glioblastoma cell line (U-87) may be decreased by increasing discharge power of the CAP. Similarly, a line 612 represents the viability of the Adenocarcinoma cell line (MDA-MB-231) at 11.5 volts over incubation time. A second line 614 represents the viability of the Adenocarcinoma cell line (MDA-MB-231) at 15.5 volts over incubation time. As shown by FIG. 6, the viability of the Adenocarcinoma cell line (MDA-MB-231) may be decreased by increasing discharge power of the CAP.

FIG. 7 are graphs that show plasma self-organization and time dependencies of ROS and RNS concentrations in liquid media treated with self-organized plasma forming stratified interface patterns. Plasma response can be monitored in real time as explained above. The cell response differs per cell type (i.e., GBM and adenocarcinoma cells) based on CAP treatment duration and applied voltage.

The graphs in FIG. 7 shows that discharge mode and plasma produced RONS for two distinct discharge modes. A first image 702 shows a low current (5 mA) plasma jet while a second image 704 shows a high current (20 mA) plasma jet. A graph 712 shows the $NO_2$ concentration and the $H_2O_2$ concentration as a function of the time the low current plasma jet is applied. A graph 714 shows the $NO_2$ concentration and the $H_2O_2$ concentration as a function of the time the high current plasma jet is applied. A graph 722 shows the viability of U86 and MDA-MB-231 cells over a 24-hour period based on the application of a low current plasma jet. A graph 724 shows the viability of U86 and MDA-MB-231 cells over a 24-hour period based on the application of a high current plasma jet.

The images 702 and 704 in FIG. 7 further show that different discharge modes are characterized by self-organized patterns on the liquid surface. Such different discharge patterns result in significant changes in composition and cell viability after plasma treatment. When the therapeutic media is processed at high current (i.e., self-organized plasma patterns are established at the plasma-liquid interface) as shown by the plasma jet in the image 704, the viability trend for both types of cells might depend on ROS more than RNS, because the highest concentration of RNS did not result into lowest cell viability as shown by the comparison between the relatively high $H_2O_2$ concentration in the graph 712 produced with low-current plasma and the relatively low $H_2O_2$ concentration in the graph 714 produced with high-current plasma.

Comparing the viability behavior for both cell types, MDA-MB-231 and U-87, incubated in the high- and low-current-activated media, indicates that the elevated ROS concentration plays a more important role than the RNS-induced apoptosis. Thus, plasma self-organization leads to alteration of plasma composition and consequently tuning effect of plasma on cells. The feedback algorithm executed by the controller 108 in FIGS. 1A-1C therefore may include tuning of the gas flow to result in greater ROS.

Figure 8:
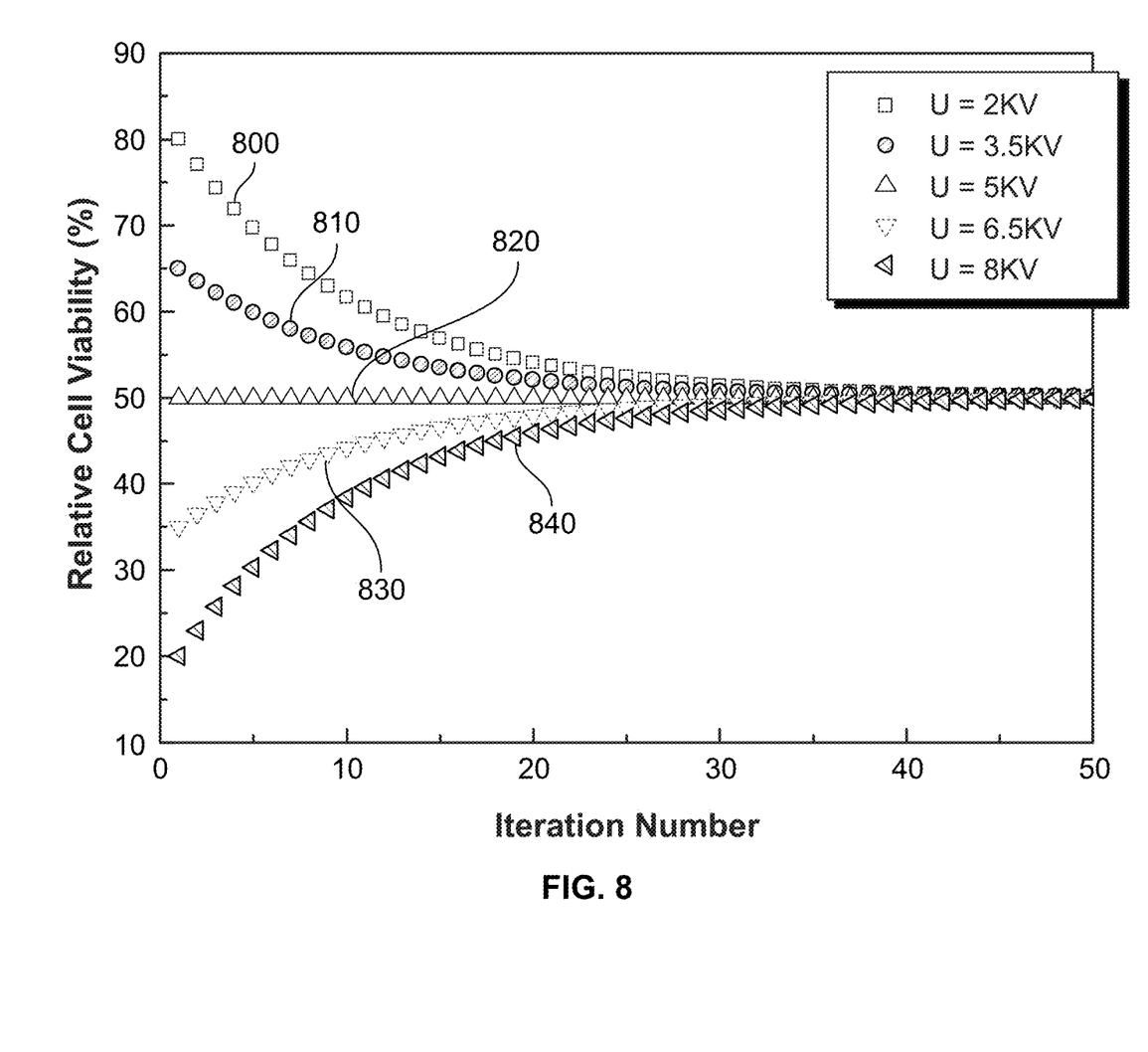
FIG. 8 is a graph showing the results of various iterative determination of the optical discharge voltage for a target viability level based on feedback from an example adaptive system.

FIG. 8 is a graph of discharge voltages over time that are adjusted using a feedback algorithm for a controller such as the controller 108 to reach a target viability level over a certain period of time. FIG. 8 shows different sets of data points 800, 810, 820, 830, and 840 that show different levels of initial discharge voltage that are adjusted over time. The set of data points 800 represents iterations from an initial discharge voltage of 2.0 kV, the set of data points 810 represents iterations from an initial discharge voltage of 3.5 kV, the set of data points 820 represents iterations from an initial discharge voltage of 5.0 kV, the set of data points 830 represents iterations from an initial discharge voltage of 6.5 kV, and the set of data points 840 represents iterations from an initial discharge voltage of 8.0 kV. In this example, the target cancer cells are measured for viability after the plasma treatment for each of the initial discharge voltages. Each of the voltages represented by the set of data points 800, 810, 820, 830, and 840 are adjusted based on the viability measurements to the target viability of 50% within a certain time period in this example. The convergence of the set of data points 800, 810, 820, 830, and 840 shows the adjustment of the initial discharge voltages by an adaptive system to the 5 kV optimal level to reach the target viability level. A similar convergence may be obtained to arrive at optimal levels for other parameters such as initial distances, initial gas flow, or initial gas composition for each different type of cell. Any level of viability may be selected for the target viability and thus be performed by the controller 108 to iteratively adjust the parameters to reach the target viability.

Figure 9:
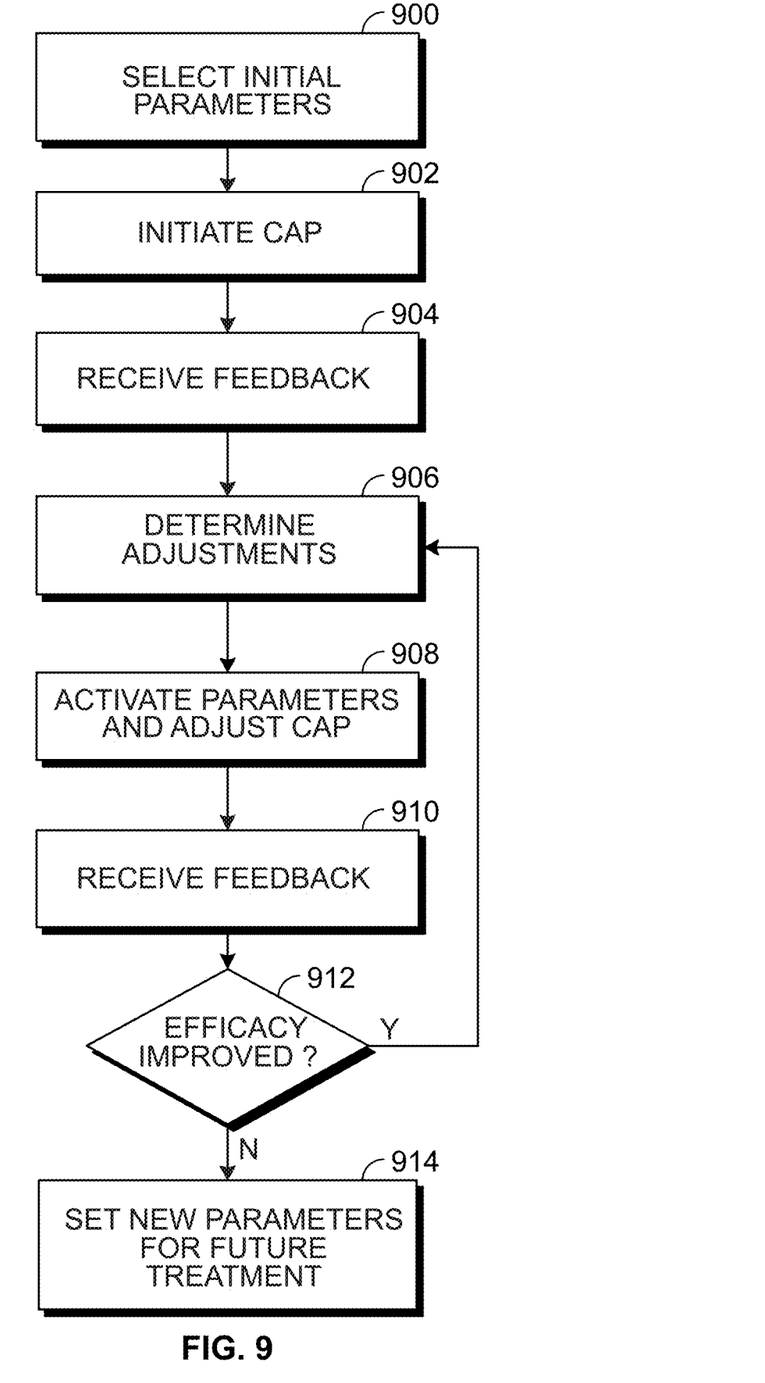
FIG. 9 is a flow diagram of the instructions executed by a controller to receive feedback data from a cold atmospheric plasma treatment and adjust the cold atmospheric plasma jet.

FIG. 9 is a flow diagram of the software instructions executed by the controller 108 in FIGS. 1A-1C to adapt the plasma jet for effective treatment of the cells. The flow diagram in FIG. 9 is representative of example machine readable instructions for the controller 108 in FIGS. 1A-1C. In this example, the machine-readable instructions comprise an algorithm for execution by: (a) a processor, (b) a controller, and/or (c) one or more other suitable processing device(s). The algorithm may be embodied in software stored on tangible media such as, for example, a flash memory, a CD-ROM, a floppy disk, a hard drive, a digital video (versatile) disk (DVD), or other memory devices. However, persons of ordinary skill in the art will readily appreciate that the entire algorithm and/or parts thereof can alternatively be executed by a device other than a processor and/or embodied in firmware or dedicated hardware in a well-known manner (e.g., it may be implemented by an application specific integrated circuit (ASIC), a programmable logic device (PLD), a field programmable logic device (FPLD), a field programmable gate array (FPGA), discrete logic, etc.). For example, any or all of the components of the interfaces can be implemented by software, hardware, and/or firmware. Also, some or all of the machine readable instructions represented by the flowchart of FIG. 9 may be implemented manually. Further, although the example algorithm is described with reference to the flowcharts illustrated in FIG. 9, persons of ordinary skill in the art will readily appreciate that many other methods of implementing the example machine-readable instructions may alternatively be used. For example, the order of execution of the blocks may be changed, and/or some of the blocks described may be changed, eliminated, or combined.

The initial parameters are selected for the plasma jet including an initial position of the jet to the area with cancer cells, discharge voltage and gas flow, and composition (900). The area of interest is injected with marker material. The controller 108 then initiates the cold plasma jet in the area of interest (902). The controller 108 then reads the feedback from the area of interest such as by sensing the luminescence level from the sensor 134 in FIG. 1A-1C (904). The controller 108 then determines adjustments based on the type of cells and determines the new parameters such as flow rate, gas composition discharge voltage, and distance of the plasma jet (906). The parameters may be selected based on an analysis of the effectiveness of the initial plasma jet. The effectiveness may indicate the type of cell and thus assist in selecting the parameter to be adjusted for increasing efficacy. For example, if viability remains at a level that is correlated with that of a certain cell such as brain cancer cells, this may indicate the selection of an increase in discharge voltage as being the most effective parameter to be adjusted.

The controller 108 then activates the parameters to adjust the plasma jet (908). The controller 108 then reads the feedback from the area of interest (910). The controller 108 determines whether efficacy has been improved (912). If efficacy has been improved, the controller 108 loops back to determine additional adjustments (906). If efficacy remains the same, the controller 108 sets the new parameters for treatment for the specific type of cell (914).

The above examples allow plasma adaptation, self-organization, and prospects of plasma medicine. The system based on plasma self-organization allows for adaptive plasma therapeutic treatments that can adjust the CAP interaction with cells and tissues through responding to boundary conditions at the plasma cell interface. The nature of the plasma adaptive therapeutic system through real time cellular and tissue response allows optimal and selective treatment. This approach can be applied to personalized plasma-based treatment of cancer and other diseases such as HIV. As a result, the application of plasma might lead to specific unique responses dependent on the person's specific genetic makeup. Thus, the same combination of reactive species and electric field applied to the body during plasma treatment might have a different effect on each person due to genome specifics.

Such an adaptive system may include new plasma sources having many modes of operation with bifurcation points. An adaptive system may also employ an efficient multiparametric feedback system based on cellular responses to improve the feedback and adjustments of the CAP. Although the above examples have been directed toward cancer cell treatments, the principles described above can be applied to any other treatments for diseased tissues such as wound healing, dental, bacterial disinfection, HIV treatment, etc., that can utilize plasma state for the treatment.

The terminology used herein is for the purpose of describing particular embodiments only, and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art. Furthermore, terms, such as those defined in commonly used dictionaries, should be interpreted as having a meaning that is consistent with their meaning in the context of the relevant art, and will not be interpreted in an idealized or overly formal sense unless expressly so defined herein.

While various embodiments of the present invention have been described above, it should be understood that they have been presented by way of example only, and not limitation. Numerous changes to the disclosed embodiments can be made in accordance with the disclosure herein, without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur or be known to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

What is claimed is:

1. A system for treatment of an area having cells, comprising:
   a plasma device to generate a cold atmospheric plasma jet directed at the area having cells;
   a sensor operable to generate a sensor signal based on sensing the viability of selected cells in the area; and
   a controller coupled to the plasma device and the sensor, the controller operative to:
      control an initial plasma jet generated by the plasma device;
      receive the sensor signal from the sensor;
      determine cell viability of the selected cells based on the sensor signal;
      executing a real-time feedback algorithm to determine whether and how to adjust the initial plasma jet to produce a modified plasma jet to change the determined cell viability to a targeted cell viability level; and
      adjust the initial plasma jet to produce the modified plasma jet in real-time.

2. The system of claim 1, wherein the selected cells are cancerous cells.

3. The system of claim 2, wherein the cancerous cells are one of brain cancer cells, breast cancer cells, pancreatic cancer cells, skin cancer cells, bladder cancer cells, colon cancer cells, or lung cancer cells.

4. The system of claim 1, wherein the plasma jet generates an oxygen or nitrogen reactive species.

5. The system of claim 1, further comprising a magnetic field generator to generate a magnetic field over the area.

6. The system of claim 1, further comprising an actuator coupled to the controller, wherein the controller is operative to control the actuator to change the position of the plasma device relative to the area.

7. The system of claim 1, further comprising a power regulator coupled to the controller, wherein the controller is operative to change a discharge voltage or a discharge current of the plasma device via the power regulator.

8. The system of claim 1, wherein the controller is operative to change gas flow or gas composition generating the plasma jet.

9. The system of claim 1, further comprising a nanoparticle injector to inject nano particles into the area.

10. The system of claim 9, wherein medication is injected with the nano-particles.

11. The system of claim 1, wherein a marker material is injected in the area.

12. The system of claim 11, wherein the sensor is a luminescence sensor coupled to the controller, the luminescence sensor in proximity to the area, wherein the marker material generates a luminesce luminescence level when attached on live cells in the area.

13. The system of claim 1, wherein the sensor is $H_2O_2$ molecule chemical probe, and wherein the sensor signal is associated with $H_2O_2$ molecules generated by the cancerous cells in the area.

14. The system of claim 13, wherein the sensor is a UV-visible spectrometer.

15. The system of claim 1, wherein the control of the initial plasma jet includes setting different parameters, and wherein the controller is further operative to select at least one of the different parameters to adjust to produce the modified plasma based on the determined cell viability.

16. The system of claim 15, wherein the different parameters are at least one of the group consisting of discharge voltage, reactive species composition, and gas flow.

17. A method of treating an area having cells, the method comprising:
   ionizing a gas via a plasma device to create an initial cold atmospheric plasma jet;
   directing the initial plasma jet toward the area having cells;
   sensing cell viability of selected cells in the area with a sensor operable to generate a sensor signal based on the viability of selected cells in the area;
   receiving the sensor signal from the sensor;
   determining cell viability of the selected cells based on the sensor signal via a controller;
   executing a real-time feedback algorithm via the controller to determine whether and how to adjust the initial plasma jet to produce a modified plasma jet to change the determined cell viability to a targeted cell viability level; and
   adjusting the initial plasma jet to produce the modified plasma jet in real-time.

18. The method of claim 17, wherein the selected cells are cancerous cells.

19. The method of claim 18, wherein the cancerous cells are one of brain cancer cells, breast cancer cells, pancreatic cancer cells, skin cancer cells, bladder cancer cells, colon cancer cells, or lung cancer cells.

20. The method of claim 17, wherein the plasma jet generates an oxygen or nitrogen reactive species.

21. The method of claim 17, further comprising generating a magnetic field over the area via a magnetic field generator.

22. A system for treatment of an area having cancerous cells, comprising:
   a plasma device to generate a cold atmospheric plasma jet directed at the area having cancerous cells;
   a marker material in the area, the marker material producing a luminescence level relative to the viability of the cancerous cells;
   a luminescence sensor to generate a sensor signal on sensing the luminescence level of the cancerous cells; and
   a controller coupled to the plasma device and luminescence sensor, the controller operative to: control an initial plasma jet generated by the plasma device; measure the luminescence of the markers in the area from the sensor signal; to determine cell viability from the initial plasma jet; execute a real-time feedback algorithm to determine whether and how to adjust the plasma jet to produce a modified plasma jet to change the determined cell viability to a targeted cell viability level; and adjust the initial plasma jet to produce the modified plasma jet in real-time.

* * * * *